United States Patent [19]

Nyéki née Kuprina et al.

[11] Patent Number: 5,041,535
[45] Date of Patent: Aug. 20, 1991

[54] ANTILEUKEMIC AND IMMUNOSTIMULANT PEPTIDES

[75] Inventors: Olga Nyéki née Kuprina; István Schon; Lajos Kisfaludy; László Dénes; György Hajós; László Szporny; Béla Szende; Károly Lapis, all of Budapest, Hungary

[73] Assignee: Richter Gedeon Vegyeszeti Gyar Rt., Budapest, Hungary

[21] Appl. No.: 123,124

[22] Filed: Nov. 20, 1987

[30] Foreign Application Priority Data

Nov. 21, 1986 [HU] Hungary .................. 4827/86

[51] Int. Cl.$^5$ .................. C07K 5/10; C07K 5/8; C07K 5/6
[52] U.S. Cl. .................. 530/330; 548/550; 530/331
[58] Field of Search .................. 514/17, 18, 19; 530/330, 331; 548/550

[56] References Cited

U.S. PATENT DOCUMENTS 4,629,723 12/1986 Goldstein et al. .................. 514/17
4,874,844 10/1989 Brunetti et al. .

FOREIGN PATENT DOCUMENTS 2597106 10/1987 France .

OTHER PUBLICATIONS

Denes et al., in *Chem. Abstracts*, "Thymopoietin Fragments . . . ", Proc. FEBS Congr., 16th 1984.

Poulson et al., (ed.), *Organic Chemistry*, 1980, pp. 1025–1031.
Fudenberg et al., *Basic & Clinical Immunology*, 1980, p. 482.
Biochem. J., 219, 345–373 (1984).
Arch. Biochem. Biophys., 242, 248–255 (1985).
Biochemistry, 20, 6195–6200 (1981).
Nature, 309, 30–33 (1984).

*Primary Examiner*—John W. Rollins
*Assistant Examiner*—S. Maebius
*Attorney, Agent, or Firm*—Herbert Dubno; Jonathan Myers

[57] ABSTRACT

The new peptides of the Formulae
(1) Glp-Lys-NH$_2$
(2) Glp-Glu-Lys-NH$_2$
(3) Arg-Lys-Glu-NH$_2$
(4) Arg-lys-Asp-NH$_2$
(5) Arg-Lys-Glu-OH
(6) Arg-Lys-Gln-OH
(7) Leu-Val-Ala-OH
(8) Arg-Orn-Asp-Val-NH$_2$
(9) Arg-Orn-Asp-Val-OH
(10) Lys-Glu-Lys-Lys-OH
(11) Lys-Leu-Lys-Lys-OH
(12) Lys-Asp-Leu-Lys-OH
(13) Glu-Leu-Val-Ala-OH and
(14) Leu-Pro-Ala-Gly-OH
and acid addition salts thereof inhibit the proliferation of leukaemic cells and exhibit immunostimulant effect.

3 Claims, No Drawings

ANTILEUKEMIC AND IMMUNOSTIMULANT PEPTIDES

This invention relates to new peptides, which inhibit the proliferation of leukaemic cells and exhibit immunostimulant effect, a process for the preparation thereof and pharmaceutical compositions comprising the said peptides. The invention also relates to a method of treatment of mammals—including humans—for inhibiting the proliferation of leukaemic cells and stimulating the immune system.

According to an aspect of the present invention there are provided new peptides of the Formulae
(1) Glp-Lys-NH$_2$
(2) Glp-Glu-Lys-NH$_2$
(3) Arg-Lys-Glu-NH$_2$
(4) Arg-Lys-Asp-NH$_2$
(5) Arg-Lys-Glu-OH
(6) Arg-Lys-Gln-OH
(7) Leu-Val-Ala-OH
(8) Arg-Orn-Asp-Val-NH$_2$
(9) Arg-Orn-Asp-Val-OH
(10) Lys-Glu-Lys-Lys-OH
(11) Lys-Leu-Lys-Lys-OH
(12) Lys-Asp-Leu-Lys-OH
(13) Glu-Leu-Val-Ala-OH and
(14) Leu-Pro Ala-Gly-OH
and acid addition salts thereof.

The new peptides of the present invention inhibit the proliferation of leukaemic cells and exhibit immunostimulant effect.

It is known [Recent Progress in Hormone Research, 37, 369–412 (1981); Cancer Immunol. Immunother. 15, 78–83 (1983)] that certain thymus hormones are capable of restoring the immune function of patients treated by cytostatic agents or irradiation and of inhibiting the proliferation of certain tumor cells. This effect can be induced with the aid of smaller hormone fragments too, the therapeutical application thereof being more favorable than that of hormones or thymus extracts having a larger molecular weight. The immunostimulant effect of hitherto synthetized smaller peptides could be unambiguously shown in various test systems (see U.S. Pat. Nos. 4,190,646, 4,215,112, 4,395,404 and 4,442,031; Hungarian patent No. 185,263 and DOS Nos. 2,938,420, 3,001,775 and 3,100,974). Thymopentine—the 32–36 fragment of thymopoietine—has already been placed on the market as a pharmaceutical active ingredient. The said known peptides induce predominantly the proliferation of T- and/or B-cells but do not inhibit directly the proliferation of tumor cells.

It is the object of the present invention to provide new thymopoietine fragment analogs, which in addition to the immunostimulant activity of known analogs aldo possess a strong antitumor effect.

It has been found in a surprising manner that the new peptides of the Formulae (1)–(14) exhibit a strong antitumor effect in addition to the immunostimulant activity. In the test system used by us the petides of the present invention exert a stronger antitumor effect than the known immunostimulant peptides serving as control, i.e. thymopentine (U.S. Pat. No. 4,190,646) and the tetrapeptide of the Formula H-Arg-Lys-Asp-Val-OH (Hungarian patent No. 185,263). Besides the aforesaid the new peptides of the present invention differ from the known cytostatic agents also in that the compounds of the invention inhibit the proliferation only of cancerous cells and do not exert a general (systemic) immunosuppressive effect.

According to a further aspect of the present invention there is provided a process for the preparation of peptides of the Formulae (1)–(14) and acid addition salts thereof.

According to the process of the present invention the new peptides of the Formulae (1)–(14) and acid addition salts thereof are prepared in solution, by stepwise sequential chain-lengthening, whereby active ester and/or mixed anhydride coupling steps and the setting free steps of α-amino group are subsequently carried out; as starting material C-terminal amino acid derivative is used, which comprises carboxy group being amidated or esterified by a hydrogenolytically or acidolytically removable group, optionally in the side-chain a protected amino group and/or a carboxy group esterified by a hydrogenolytically or acidolytically removable group, and a free α-amino group; thus protected derivatives of the peptides of the Formulae (1)–(14) are prepared which are esterified or amidated on the carboxy group and bear a Boc or Z protecting group on the amino groups not participating in the peptide bond;

whereupon the protecting groups present are removed by hydrogenolysis and/or acidolysis, and if desired, the free peptides of the Formulae (1)–(14) thus obtained are converted into the acid addition salts thereof by reacting with an acid.

In the course of the synthesis a combination of protecting groups is used which enables the selective removal of the protecting group of the amino group and at the end of the synthesis the splitting of all the protecting groups, if possible in a single step. The peptide bond is formed by using the pentafluoro phenyl ester method disclosed in Hungarian patent No. 168,431 or the mixed anhydride procedure described in Hungarian patent No. 183,579.

The amino groups are preferably protected with the aid of a Boc or Z group, while the protection of the carboxy groups is accomplished preferably by esterifying with tertiary butyl alcohol, benzyl alcohol or nitrobenzyl alcohol.

From the synthesized and protected peptide thus obtained the protecting groups optionally present are removed after the synthesis, whereupon the free peptide thus obtained is converted into an acid addition salt by treatment with an acid. The protecting groups are preferably removed by catalytic hydrogenation or acidolysis carried out with an acid.

The free peptides thus obtained are generally sufficiently pure for use in therapy and no further purification is required. The peptides can be, however, purified, if necessary, by known methods e.g. by chromatography on a silica column. Peptides obtained in the form of a solution can be generally isolated by evaporating the solution or by means of lyophilization.

The biological activity of the peptides according to the present invention is tested by the following methods.

1) Inhibition of the proliferation of tumor cells

In the test human K-562 erythroleukaemical cell-line is used (Karolinska Institute, Stockholm). Incubation is carried out in a nutrient medium designated RPMI-1640 (manufactured by Flow, Great Britain) comprising 10% of foetal calf serum, at a temperature of 37° C., in a humidified incubator containing 3% of carbon dioxide, in plastic dishes. Every point of measurement corresponds to the average of the data measured in three dishes, each. At the beginning of the test the dilution amounts to $0.5 \times 10^5$ cells/ml. Treatment is carried out 24 hours after dilution in a manner that the medium is not changed after the treatment. The cells are counted for 96 hours after dilution every 24th hour wit the aid of a Buerker chamber.

Under the effect of the peptide in the 24th hour after treatment the cell number stagnates and later it increases to a very small extent. This indicates that the peptide exhibits a cell-division inhibiting activity rather than a cell-killing effect. The tumor-cell division inhibiting effect of the new peptides is summarized in Table 1 (72 hours after treatment). The rate of inhibition is expressed in the percentage of the control. It clearly appears from the data of the Table that the tested peptides inhibit the proliferation of human K-562 erythroleukaemic cells.

TABLE 1

Inhibition of the proliferation of K-562 cells, in the 72nd hour after treatment with the peptide, expressed in the percentage of the control

| Concentration of the peptide | inhibition (c %) | |
|---|---|---|
| | 10/ug/ml | 1/ug/ml |
| Tested peptide | | |
| 1. Glp—Lys—NH$_2$ | 42 | 20 |
| 2. Glp—Glu—Lys—NH$_2$ | 55 | 40 |
| 3. Arg—Lys—Glu—NH$_2$ | 52 | 40 |
| 4. Arg—Lys—Asp—NH$_2$ | 50 | 25 |
| 5. Arg—Lys—Glu | 48 | 40 |
| 6. Arg—Lys—Gln | 30 | 25 |
| 7. Leu—Val—Ala | 52 | 38 |
| 8. Arg—Orn—Asp—Val—NH$_2$ | 51 | 35 |
| 9. Arg—Orn—Asp—Val | 54 | 35 |
| 10. Lys—Glu—Lys—Lys | 40 | 28 |
| 11. Lys—Leu—Lys—Lys | 70 | 65 |
| 12. Lys—Asp—Leu—Lys | 55 | 40 |
| 13. Glu—Leu—Val—Ala | 65 | 55 |
| 14. Leu—Pro—Ala—Gly | 70 | 45 |
| A. Arg—Lys—Asp—Val—Tyr (TP 5) | 32 | |
| B. Arg—Lys—Asp—Val (TP 4) | 4 | |

Peptides "A" and "B" are known reference compounds (Hungarian Pat. No. 185,263).

2. Inhibitions of proliferation of T-lymphocytes

Inhibition of the proliferation of T-lymphocytes is tested in the E-rosetta test inhibited by Azathioprine [6-(1-methyl-4-nitroimidazole-5-yl-thio)-purine; Thymus 1, 195 (1980)].

To 200 µl of a healthy lymphocyte cell-suspension 500 µl/ml of Azathioprine and 200 µl of a separate dilution of the test compound in HBBS buffer (manufacturer: Flow, Great Britain) are added (concertration range: $10^{-3}$ to $10^{11}$ mole/l). The mixture is incubated at a temperature of 37° C. in air containing 5% of carbon dioxide for 60 minutes, whereupon 200 µl of a 1% sheep erythrocyte suspension are added. The mixture thus-obtained is centrifuged at 1,000 r.p.m. for 5 minutes, the supernatant is removed by decanting and in the suspension the lymphocytes forming E-rosetta are counted under a microscope from at least 400 cells.

Under the effect of the peptides the E-rosetta forming activity of the lymphocytes inhibited by Azathioprine increases to different extent. In the tested dose range the peptides do not inhibit the E-rosetta forming activity of lymphocytes. The results are summarized in Table 2. The data show the extent to which the peptides relieve the inhibition (R %) exerted by Azathioprine on the E-rosetta forming activity of lymphocytes. It appears from the data of Table 2 that the tested peptides increase the E-rosetta forming capacity of inhibited lymphocytes, i.e. the peptides of the present invention show immunostimulant effect.

TABLE 2

Restoration of the E-rosetta forming activity of lymphocytes inhibited by Azathioprine

| Peptide concentration | Relief of inhibition (R %) $10^{-N}$ mole/l | | | | |
|---|---|---|---|---|---|
| Value of N | 11 | 9 | 7 | 5 | 3 |
| Tested peptide | | | | | |
| 1. Glp—Lys—NH$_2$ | 10.0 | 25.0 | 36.6 | 9.9 | 33.0 |
| 2. Glp—Glu—Lys—NH$_2$ | 37.1 | 24.3 | 31.7 | 20.2 | 25.4 |
| 3. Arg—Lys—Glu—NH$_2$ | 17.0 | 24.8 | 15.6 | 22.6 | 24.3 |
| 4. Arg—Lys—Asp—NH$_2$ | 18.5 | 23.9 | 18.7 | 30.0 | 29.7 |
| 5. Arg—Lys—Glu | 27.5 | 24.0 | 24.7 | 24.6 | 24.5 |
| 6. Arg—Lys—Gln | 34.5 | 26.3 | 27.0 | 27.4 | 26.2 |
| 8. Arg—Orn—Asp—Val—NH$_2$ | 24.5 | 34.4 | 22.0 | 33.5 | 36.7 |
| 9. Arg—Orn—Asp—Val | 23.8 | 21.3 | 17.8 | 18.9 | 21.9 |
| 10. Lys—Glu—Lys—Lys | 26.6 | 21.1 | 25.2 | 16.3 | 22.9 |
| 11. Lys—Leu—Lys—Lys | 45.1 | 33.6 | 28.8 | 36.8 | 35.8 |
| 12. Lys—Asp—Leu—Lys | 8.6 | 8.9 | 16.5 | 21.9 | 13.7 |
| A. Arg—Lys—Asp—Val—Tyr (TP 5) | 19.4 | 30.0 | 38.7 | 29.3 | 31.7 |
| B. Arg—Lys—Asp—Val (TP 4) | 34.0 | 32.5 | 46.4 | 35.4 | 35.4 |

Peptides "A" and "B" are known reference compounds $$R \% = \frac{(EXP\text{-}ERFC - AZ\text{-}ERFC)}{ERFC - AZ\text{-}ERFC} \times 100\%$$

ERFC = number of lymphocytes forming E-rosetta, without the addition of Azathioprine;

AZ-ERFC = number of lymphocytes forming E-rosetta, on addition of Azathioprine;

EXP-ERFC = number of lymphocytes forming E-rosetta, in the presence of Azathiprine and the tested peptide.

3. Effect on antibody production in mice

The effect on in vivo antibody production is tested on CELP mice treated with a 100 mg/kg body weight dose of cyclophosphamide {2-[bis-(2-chloroethyl)-amino]-tetrahydro-2H-1,3,2-oxaza -phosphorine-2-oxide; method: Z. Naturforsch. 35B, 1476 (1980)}. The mice are intraperitoneally immunized with a 1% sheep erythrocyte suspension previously washed three times with a 0.9% sodium chloride solution after 10 minutes of centrifuging at 2,500 r.p.m. Simultaneously with immunization carried out on the 0. day, the activity of the immune system is suppressed by means of treatment with a 100 mg/kg i.p. does of cyclophosphamide. On the 3rd day of the test the peptides are administered to the animals intraperitoneally in a dose of 5, 50 and occasionally 100 mg/kg respectively. On the 6th day of the test blood is taken retroorbitally from the mice and the anti-sheep erythrocyte titer of the serum is determined. The definitely inhibited state of the suppressed immune system is chosen as starting time of treatment of the peptides. The effect of the peptides is expressed as percentage of the relief of inhibition (G %). The data are disclosed in Table 3.

It can be seen from the data of Table 3 that the peptides of the present invention stimulate the immune system inhibited by cyclophosphamide to different extent in CELP mice. The new compounds of the present invention do not show the immunosuppressive effect characteristic of cytostatic agents.

TABLE 3

Relief of inhibition in mice having antibody production inhibited by cyclophosphamide (G %)

| Dose of peptides (mg/kg) | Restoration of primary immune answer, G % | | |
|---|---|---|---|
| | 100 | 50 | 5 |
| Tested peptides | | | |
| 1. Glp—Lys—NH₂ | | 133.3 | 123.8 |
| 2. Glp—Glu—Lys—NH₂ | | 3.0 | 23.0 |
| 3. Arg—Lys—Glu—NH₂ | | 47.6 | 78.1 |
| 4. Arg—Lys—Asp—NH₂ | 28.5 | | |
| 5. Arg—Lys—Glu | | 76.9 | 61.5 |
| 6. Arg—Lys—Gln | 14.8 | | |
| 7. Leu—Val—Ala | | 100.0 | 73.3 |
| 8. Arg—Orn—Asp—Val—NH₂ | | 28.0 | |
| 9. Arg—Orn—Asp—Val | 23.8 | | |
| 10. Lys—Glu—Lys—Lys | | 37.7 | 15.5 |
| 11. Lys—Leu—Lys—Lys | | 80.7 | 38.4 |
| 12. Lys—Asp—Leu—Lys | | 53.8 | 38.4 |
| 13. Glu—Leu—Val—Ala | | 32.8 | 20.9 |
| 14. Leu—Pro—Ala—Gly | | 56.8 | 34.0 |

$$G \% = \frac{Control - Test}{Control - CFY} \times 100$$

Control = antibody production of untreated animals which receive no test compound;
Test = antibody production of treated animals which receive test compound,
CFY = antibody production of animals treated with 100 mg/kg of cyclophosphamide.

4. Dermatitis test induced with oxazolone

In this test a modified pharmacological model of D. P. Evans et al. [Br. J. Pharmac. 43, 403-488 (1971)] is used.

The abdominal skin of male CFLP mice weighing 20-22 g is painted after the removal of the hair with 0.1 ml of a 2% solution of oxazolon (4-ethoxymethyl-2-phenyl-oxazoline, manufacturer Sigma) in sunflower oil. On the right ear of the test animals 7 days after sensitization (painting) inflammatory reaction is induced with the aid of 10 μl of a 2% acetonous oxazolone solution and simultaneously the animals are treated with a 1 or 2 mg/kg, respectively, i.p. does of the test compound. The test compound is dissolved in a physiological sodium chloride solution in such a concentration that the active ingredient content corresponding to the dose should be dissolved in a volume of 0.5 ml/10 g animal body weight.

The antiinflammatory effect is determined as follows: the animals are sacrificed in the 24th hour after treatment, whereupon the right and left ears are cut off. The percentual weight increase of the right ear related to the left ear is characteristic of the rate of inflammation induced during the test, while the percentual reduction of weight increase of the treated animals related to the untreated control is proportional to the antiinflammatory effect. In Table 4 the reduction of weight increase (antiinflammatory effect) achieved by the test compounds is disclosed, as the percentage of the untreated control.

TABLE 4

Inhibition of inflammation induced by oxozolone, in the 24th hour after treatment with the peptides

| Dose of peptide | inhibition as % of control | |
|---|---|---|
| | 1 mg/kg | 2 mg/kg |
| Tested peptides | | |
| Glp—Lys—NH₂ | 62 | 61 |
| Arg—Lys—Asp—NH₂ | 27 | |
| Lys—Glu—Lys—Lys—OH | 22 | 79 |
| Lys—Leu—Lys—Lys—OH | 30 | 41 |
| Glu—Leu—Val—Ala—OH | 40 | |
| Leu—Pro—Ala—Gly—OH | 55 | |

5. Effect on phagocytosis, in vivo

Male CFLP mice having a body of weight of 22-23 g are divided into four groups of 8-12 animals each. The animals of the test groups are treated with Glp-Lys-NH₂-mandelate for 2 days. The treatment is carried out by administering a 0.1, 1 or 10 mg/kg s.c. dose, respectively, of the active ingredient once a day, in the form of a solution in a physiological sodium chloride solution. In the 24th hour after the last treatment the yeast cell incorporating capacity of the peritoneal exsudatum cells (PEC) is determined. The results obtained are set forth in Table 5. In the Table the $\bar{x} \pm S.E.M.$ data relate to the number of yeast cells incorporated into the 100 PEC cells.

TABLE 5

PEC phagocytating activity of PEC in the 24th hour after treatment

| Phagocyte activity | $\bar{x} \pm S.E.M.$ | | | |
|---|---|---|---|---|
| Dose (mg/kg) | 0.0 | 0.1 | 1.0 | 10 |
| | 179.7 ± 3.6 | 182.3 ± 3.5 | 209.3 ± 8.6 | 244.8 ± 4.3 |
| Student's t-test: | | | $p > 0.05$ | $p > 0.01$ |

6. Determination of the effect on phagocytosis inhibited by cyclophosphamide (CY)

a) Simultaneously administered cyclophosphamide and peptide

Male CFLP mice weighing 22-23 g are divided into five groups of 8-12 animals each. The animals belonging to the test groups (all groups except the control one) are treated for two days once a day with a 80 mg/kg p.o. dose of cyclophosphamide and the animals of three of the said groups are treated simultaneously with the administration of cyclophosphamide with a 0.1, 1.0 and 10 mg/kg s.c. dose, respectively, of Glp-Lys-NH₂-mandelate dissolved in a physiological soidum chloride solution. On the 3rd day of the test the yeast cell incorporating capacity of the PEC cells is determined. The results thus-obtained are summarized in Table 5. The $\bar{x} \pm S.E.M.$ values disclosed in the Table stand for the number of yeast cells incorporated by the 100 PEC cells.

TABLE 6

Phagocitizing activity of PEC in the 24th hour after treatment

| Phagocyte activity | $\bar{x} \pm S.E.M.$ | | | | |
|---|---|---|---|---|---|
| CY dose (mg/kg) | 0.0 | 80 | 80 | 80 | 80 |
| Dose (mg/kg) | 0.0 | 0.0 | 0.1 | 1.0 | 10 |
| | 186.3 ± 7.8 | 102.5 ± 4.8 | 241.7 ± 20.3 | 215.2 ± 21.5 | 164.4 ± 13.8 |

TABLE 6-continued

| | Phagocitizing activity of PEC in the 24th hour after treatment |
|---|---|
| Student's t-test | p >0.05 | b) Non-simultaneously administered cyclophosphamide and peptide

One proceeds as described in test a) except that the peptide is administered to the animals 6 hours after treatment with cyclophosphamide. The test is evaluated as described above. The results are disclosed in Table 7.

TABLE 7

| | Phagocytizing activity of PEC in the 24th hour after treatment | | | | |
|---|---|---|---|---|---|
| Phagocyte activity | | | $\bar{x} \pm$ S.E.M. | | |
| CY dose (mg/kg) | 0.0 | 80 | 80 | 80 | 80 |
| Dose (mg/kg) | 0.0 | 0.0 | 0.1 | 1.0 | 10 |
| | 221 ± 9.4 | 112.1 ± 6.4 | 226.5 ± 8.8 | 252.2 ± 7.4 | 257.3 ± 9.3 |
| Student's t-test | | | | | p >0.05 |

7. Tumor metastasis inhibiting effect 20 g male $C_{57}B_1$ mice divided into groups consisting of 5 animals each, are injected with a Lewis Lung Tumor (LLT) cell-suspension. The said cell-suspension is administered into the tail vein, in a dose of $10^5$ cells/mouse. Twenty-four hours after the administration of the tumor-cells the animals are treated with a single 10 mg/kg i.p. dose of the test compound. On the 18th day following infection with the tumor the animals are sacrificed and the cancer noduli appearing in the lungs are counted under a stereomicroscope. Animals not treated with peptide serve as control. In Table 8 the results obtained with Glp-Lys-NH$_2$ dipeptide amide are disclosed.

TABLE 8

| | No. of metastases in the lungs | | | | |
|---|---|---|---|---|---|
| Serial No. of the animals: | 1 | 2 | 3 | 4 | 5 |
| In treated animals: | 0 | 2 | 1 | 2 | 5 |
| In untreated control: | 15 | 20 | 16 | 12 | 11 |

According to a further aspect of the present invention there are provided pharmaceutical compositions comprising as active ingredient at least one peptide of the Formulae (1)–(14) of the present invention or an acid addition salt thereof in admixture with suitable inert pharmaceutical carriers. The pharmaceutical compositions of the present invention can be used in therapy for the treatment of tumorous diseases. The advantage of the use of the new compounds of the present invention resides not only in the inhibition of the proliferation of cancerous cells but also in the fact that contrary to the immunosupressive effect of known and widespreadly used cytostatic agents they exhibit a slight immunostimulant effect which maintains the defensive ability of the immune system of organism.

The peptides of the Formulae (1)–(14) and salts thereof are formulated in forms generally used in therapy by methods of pharmaceutical industry known per se. The pharmaceutical compositions of the present invention may be formulated in solid or liquid forms and may contain generally used conventional carriers, diluents, stabilizing agents, salts for modifying the osmotic pressure, agents for adjusting the pH value and/or further additives and/or auxiliary agents.

The solid pharmaceutical compositions may be e.g. powder ampoules useful in the preparation of injections. The liquid compositions may be injections and infusions.

The pharmaceutical compositions of the present invention are administered in an amount which contains sufficient active ingredient to exhibit the desired effect. The said dose depends on the severeness of the disease, the body weight of the patient and his (or her) sensitivity against the active ingredient, the mode of application the daily number of treatments etc. The dose to be applied can be safely determined by the physician based on all circumstances of the given case.

In order to enable simple administration, the active ingredient is preferably finished in the form of dosage units which contain the active ingredient in the amount to be administered or a small multiple or part (e.g. half, one-third, one-fourth part) thereof.

The pharmaceutical compositions of the present invention may generally contain from about 1 mg to about 100 mg of the active ingredient per dosage unit. The above values are naturally of a mere illustrative character and the actual active ingredient content can be below or above the said limits as well.

Further details of the present invention are to be found in the following Examples without limiting the scope of protection to the said Examples.

The abbreviations appearing throughout the specification correspond to the symbols generally used and accepted in the art [Biochem. J. 219, 345 (1984)]. All the amino acids are of a "L" configuration.

The melting points are determined in a dr. Tottoli type apparatus (Büchi, Switzerland). The thin layer chromatography values are measured on a pre-manufactured silicagel adsorbent (DC-Fertigplatten, Merck) in the following solvent mixtures:
1. ethyl acetate: stock solution=19:1
2. ethyl acetate: stock solution=9:1
3. ethyl acetate: stock solution=4:1
4. ethyl acetate: stock solution=7:3
5. n-butanol: stock solution=3:7
6. n-butanol: acetic acid: ethyl acetate: water=1:1:1:1.

The stock solution is a 20:6:11 mixture of pyridine, acetic acid and water. The above ratios are volume ratios.

The chromatograms are developped with ninhydrine and after chlorination with a KI-tolidine reactant.

Specific optical rotation is determined with the aid of a Perkin-Elmer 141 type polarimeter. The removal of the solvents and all evaporation steps are carried out in

EXAMPLE 1

Z-Lys(Z)-Glu(OBzl)-Lys(Z)-Lys(Z)-ONB

To a solution of 1.13 g (2.5 millimoles) of H-Lys(Z)-ONB-hydrochloride in 10 ml of dimethyl formamide 0.35 ml (2.5 millimoles) of triethyl amine and 1.50 g (2.8 millimoles) of Boc-Lys(Z)-OPfp are added. The reaction mixture is stirred at room temperature for 30 minutes, evaporated and the residual oil is suspended in ethyl acetate. The suspension is washed twice with 15 ml of 10% of citric acid, a 5% sodium hydrogen carbonate solution and water each. The organic phase is dried over sodium sulfate and evaporated. The protected dipeptide ester Boc-Lys(Z)-Lys(Z)-ONB thus obtained ($R^5_f=0.70$) is reacted with 10 ml of a dioxane solution containing 8 mole/l of hydrogen chloride for 15 minutes and the reaction mixture is diluted with 50 ml of anhydrous ether. The precipitated free dipeptide ester hydrochloride Lys(Z)-Lys(Z)-ONB.HCl ($R^3_f=0.30$) is filtered off, washed with ether and dissolved in 15 ml of dimethyl formamide. The pH of the solution is adjusted to 8 with triethyl amine, whereupon 1.5 g (3.0 millimoles) of Boc-Glu(OBzl)-OPfp are added. The reaction mixture is stirred at room temperature for 30 minutes, evaporated and the residue is suspended in 50 ml of ethyl acetate. The suspension is washed twice with 15 ml of aqueous hydrochlorid acid (1 mole/l), a 5% sodium hydrogen carbonate solution and water, each. The organic phase is dried over anhydrous sodium sulfate and evaporated. The oily residue is solidified with anhydrous ether, the suspension thus obtained is filtered and the precipitate is washed with ether. Thus the protected tripeptide ester Boc-Glu(OBzl)-Lys(Z)-Lys(Z)-ONB is obtained ($R^5_f=0.85$). The protected tripeptide ester thus obtained is reacted with 15 ml of dioxane containing 8 mole/l of hydrogen chloride for 15 minutes and the reaction mixture is diluted with 100 ml of anhydrous ether. The precipitated free tripeptide ester hydrochloride Glu(OBzl)-Lys(Z)-Lys(Z)-ONB.HCl is filtered, washed with ether and dissolved in 20 ml of dimethyl triethyl amine and to the suspension 1.45 g (2.5 millimoles) of Z-Lys(Z)-OPfp are added. The reaction mixture is stirred at room temperature for 15 minutes whereby the pH of the solution is kept at a value of about 8 by adding triethyl amine. The reaction mixture is treated with 60 ml of ethyl acetate and the mixture thus obtained is washed twice with 15 of aqueous hydrochloride acid (concentration 1 mole/l) and water, each. The organic phase is dried over anhydrous sodium sulfate and evaporated in vacuo. The oily residue is solidified with ethyl acetate. The precipitated protected tetrapeptide ester (2.4 g) Boc-Lys(Z)-Glu(OBzl)-Lys(Z)-Lys(Z)-ONB is filtered off and recrystallized from 25 ml of ethyl acetate. Thus 2.0 g of the desired compound are obtained, yield 62% (related to the Lys(Z)-ONB.HCl starting material). M.p.: 140–142° C., $R^5_f=0.70$.

EXAMPLE 2

Boc-Arg(HCl)-Lys(Boc)-Glu(O'Bu)-NH₂

1.46 g (5.0 millimoles) of Glu(O'Bu)-NH₂-oxalate and 2.73 g (65.0 millimoles) of Z-Lys(Boc)-OPfp are dissolved in 10 ml of dimethyl formamide, whereupon 2.10 ml (15 millimoles) of triethyl amine are added dropwise at room temperature. After an hour the reaction mixture is evaporated in vacuo the residue is dissolved in a mixture of 50 ml of ethyl acetate and 50 ml of chloroform. The organic phase is washed three times with 40 ml of aqueous hydrochloric acid (concentration 1 mole/l) and three times with a 5% sodium hydrogen carbonate solution each, dried over anhydrous sodium sulfate and evaporated. The protected crude dipeptide amide Z-Lys(BOC)-Glu(O'Bu)-NH₂ thus obtained is dissolved in 100 ml of ethanol and hydrogenated in the presence of 0.5 g of a 10% palladium-charcoal catalyst and stirring by bubbling hydrogen through the solution. The progress of the reaction is monitored by thin layer chromatography (the $R_f$ value of the protected dipeptide amide is 0.85 and that of the dipeptide amide amounts to 0.10, in solvent mixture No. 3). The protecting group is completely removed within 2 hours. The suspension is filtered, the filtrate is evaporated and the residual Lys(Boc)-Glu(O'Bu)-NH₂ free dipeptide amide is dissolved in 15 ml of dimethyl formamide.

In an other flask 1.80 g (5.5 millimoles) of Z-Arg(HCl)-OH.H₂O are dissolved in 15 ml of dimethyl formamide. To this solution 0.77 ml (5.5 millimoles) of triethyl amine is added, and the mixture is cooled to −10° C. At this temperature to the mixture 0.71 ml (5.5 millimoles) of isobutyl chloro formiate is added. The solution of the mixed anhydride thus obtained is stirred for a further period of 10 minutes at this temperature and the above-mentioned dimethyl formamide solution of the free dipeptide amide is added at the same temperature. The reaction mixture is stirred at room temperature overnight and evaporated in vacuo. The residual oil is dissolved in a mixture of 100 ml of chloroform and 10 ml of n-butanol, the solution is washed three times with a 5% acetic acid solution and three times with a 5% sodium hydrogen carbonate solution, dried over anhydrous sodium sulfate and evaporated in vacuo. The residual oil is dissolved in 10 ml of ethyl acetate and ether is added until the solution becomes cloudy. The suspension thus obtained is allowed to stand in a refrigerator filtered and the precipitate is dried. Thus 1.94 g of the desired compound are obtained, yield 53.7%. M.p.: 86–88° C.; $[\alpha]^{20}_D=-15.8°$ (c=1, dimethyl formamide), $R^3_f=0.30$.

The following peptide derivatives are prepared in an analogous manner to Examples 1 and 2.

| Compound | Example | Yield (%) | M.p. °C. | $R_f$ | Purification |
| --- | --- | --- | --- | --- | --- |
| Z—Gln—Lys(Z)—NH₂ | 1 | 72 | 209–212 | 0.43(3) | EtOH |
| Z—Gln—Glu(OBzl)—Lys(Z)—NH₂ | 1 | 53 | 180 (b) | 0.65(4) | MeOH |
| Boc—Arg(HCl)—Lys(Boc)—Glu(O'Bu)—NH₂ | 2 | 54 | 86–88 | 0.30(3) | EtOAc-ether |
| Boc—Arg(HCl)—Lys(Boc)—Asp(O'Bu)—NH₂ | 2 | 47 | 79–81 | 0.25(4) | ether |
| Boc—Arg(HCl)—Lys(Boc)—Glu(O'Bu)—O'Bu | 2 | 28 | amorphous | 0.70(4) | col. chr. |
| Boc—Arg(HCl)—Lys(Boc)— | 2 | 27 | amorphous | 0.40(4) | col. chr. |

-continued

| Compound | Example | Yield (%) | M.p. °C. | $R_f$ | Purification |
|---|---|---|---|---|---|
| Gln—O$^t$Bu | | | | | |
| Boc—Leu—Val—Ala—ONB | 1 | 85 | 180–182 | 0.90(2) | EtOAc-hex. |
| Z—Arg(Z$_2$)—Orn(Z)—Asp(OBzl)—Val—NH$_2$ | 1 | 76 | 188–190 | 0.70(2) | EtOH |
| Z—Arg(HCl)—Orn(Z)—Asp(OBzl)—Val—OBzl | 1 | 38 | 138–141 | 0.40(4) | col. chr. |
| Z—Lys(Z)—Glu(OBzl)—Lys(Z)—Lys(Z)—ONB | 1 | 62 | 140–142 | 0.70(1) | EtOAc |
| Z—Lys(Z)—Leu—Lys(Z)—Lys(Z)—ONB | 1 | 72 | 137–139 | 0.70(1) | EtOAc |
| Z—Lys(Z)—Asp(OBzl)—Leu—Lys(Z)—ONB | 1 | 58 | 178–180 | 0.80(1) | EtOAc |
| Boc—Glu(OBzl)—Leu—Val—Ala—ONB | 1 | 79 | amorphous | 0.85(2) | petr. eth. |
| Z—Leu—Pro—Ala—Gly—ONB | 1 | 62 | oil | 0.90(2) | — |

The following abbreviations are used:
Example = No. of the analogous Example referred to;
Yield = yield obtained;
$R_f$ = $R_f$ value, in parentheses the number of the developing solvent mixture;
Purification = method of purification, including EtOH = ethanol;
MeOH = methanol;
EtOAc = ethyl acetate;
ether = diethyl ether;
hex. = n-hexane;
petr. eth. = petroIether;
col. chr. = column chromatography.

EXAMPLE 3

Lys-Glu-Lys-Lys-diacetate 1.7 g (1.3 millimoles) of Z-Lys(Z)-Glu(OBzl)-Lys(Z)-Lys(Z)-ONB protected tetrapeptide (Example No. 1) are dissolved in 30 ml of a 90% acetic acid solution. To the solution 1.0 g of a 5% palladium/charcoal catalyst are added and hydrogen is bubbled through the mixture for 6 hours. The catalyst is filtered off and the filtrate is evaporated in vacuo. To the residue 20 ml of water are added and the mixture is evaporated again. To the residue 20 ml of ethanol are added and the mixture is evaporated again. Thus at first the trace of acetic acid and then the residual water is removed. The residue thus obtained is solidified with 20 ml of a 2:3 mixture of ethanol and ether, the suspension obtained is filtered, the precipitate is washed with the above solvent mixture twice and dried over phosphorous pentoxide in a desiccator in vacuo. Thus 0.75 g of the desired compound are obtained, yield 88%. Amino acid analysis: Lys=2.95 (3.0), Glu=1.00 (1.0). $[\alpha]^{20}_d = 17.3°$ (c=1, in 10% acetic acid), $R^6_f$=0.17.

EXAMPLE 4

Arg-Lys-Glu-NH$_2$-acetate 1.47 g (2.0 millimoles) of the protected tripeptide Boc-Arg(HCl)-Lys(Boc)-Glu(O$^t$Bu)-NH$_2$ are dissolved in 15 ml of trifluoroacetic acid. The solution is allowed to stand at room temperature for one hour and a half and diluted with 150 ml of anhydrous ether. The suspension thus obtained is filtered, the precipitate is dissolved in 50 ml of water and the solution is treated with 50 ml of a DOWEX 2 ×8 anion exchange resin (acetate phase). After 15 minutes the suspension is filtered, the filtrate is clarified with activated charcoal, filtered again and lyophylized. Thus 0.93 g of the amorphous desired compound are obtained, yield 84.6%, $[\alpha]^{20}_D = -3.9$ (c=1, water).

The following peptide derivatives are prepared in an analogous manner to Examples 3 and 4.

| Compound | Example | Yield (%) | $R_f$ | $[\alpha]_D^{22}$ [°] |
|---|---|---|---|---|
| Glp—Lys—NH$_2$—mandelate$^x$ | 3 | 60 | 0.24(6) | +32.8 (a) |
| Glp—Glu—Lys—NH$_2$—acetate | 3 | 80 | 0.24(6) | −31.2 (b) |
| Arg—Lys—Glu—NH$_2$—diacetate | 4 | 85 | 0.10(5) | −3.9 (a) |
| Arg—Lys—Asp—NH$_2$—diacetate | 4 | 80 | 0.10(5) | +5.1 (a) |
| Arg—Lys—Glu—acetate | 4 | 71 | 0.05(5) | +5.9 (c) |
| Arg—Lys—Gln—diacetate | 4 | 85 | 0.05(%) | +3.3 (a) |
| Leu—Val—Ala | 3 | 66 | 0.62(6) | −35.4 (b) |
| Arg—Orn—Asp—Val—NH$_2$—diacetate | 3 | 94 | 0.10(5) | −16.5 (a) |
| Arg—Orn—Asp—Val—acetate | 3 | 74 | 0.10(5) | −16.5 (a) |
| Lys—Glu—Lys—Lys—diacetate | 3 | 88 | 0.17(5) | −17.3 (b) |
| Lys—Leu—Lys—Lys—triacetate | 3 | 80 | 0.30(5) | −19.6 (b) |
| Lys—Asp—Leu—Lys—acetate | 3 | 72 | 0.15(6) | −32.6 (b) |
| Glu—Leu—Val—Ala | 3 | 72 | 0.60(6) | −59.4 (b) |
| Leu—Pro—Ala—Gly | 3 | 65 | 0.37(6) | −117.0 (b) |

The letters in parentheses after the specific optical rotation data have the following meaning:
(a): c = 1, in water;
(b): c = 1, in 10% acetic acid;
(c): c = 1, in acetic acid.
x: the melting point of Glp—Lys—NH$_2$—mandelate amounts to 159–162° C.

What we claim is:
1. A peptide selected from the group consisting of:
Glp-Lys-NH$_2$,
Glp-Glu-Lys-NH$_2$,

Leu-Val-Ala-OH,
Arg-Orn-Asp-Val-NH$_2$,
Arg-Orn-Asp-Val-OH,
Lys-Glu-Lys-Lys-OH,
Lys-Leu-Lys-Lys-OH,
Lys-Asp-Leu-Lys-OH,
Glu-Leu-Val-Ala-OH, and
Leu-Pro-Ala-Gly-OH,
or a pharmaceutically acceptable acid addition salt thereof.

2. A peptide of claim 1 selected from the group consisting of:

Glp-Lys-NH$_2$,
Glp-Glu-Lys-NH$_2$,
Leu-Val-Ala-OH,
Lys-Glu-Lys-Lys-OH,
Lys-Leu-Lys-Lys-OH,
Lys-Asp-Leu-Lys-OH,
Glu-Leu-Val-Ala-OH, and
Leu-Pro-Ala-Gly-OH,
or a pharmaceutically acceptable acid addition salt thereof.

3. Lys-Leu-Lys-Lys-OH or a pharmaceutically acceptable acid addition salt thereof as defined in claim 1.

* * * * *